United States Patent
Spies et al.

(10) Patent No.: US 8,280,130 B2
(45) Date of Patent: Oct. 2, 2012

(54) METHOD TO INDIVIDUALIZE KINETIC PARAMETER ESTIMATION FOR DYNAMIC MOLECULAR IMAGING PROCEDURES

(75) Inventors: Lothar Spies, Hamburg (DE); Manoj Narayanan, Snohomish, WA (US); Bart Jacob Bakker, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 909 days.

(21) Appl. No.: 12/293,614

(22) PCT Filed: Mar. 19, 2007

(86) PCT No.: PCT/IB2007/050942
§ 371 (c)(1),
(2), (4) Date: Sep. 19, 2008

(87) PCT Pub. No.: WO2007/107946
PCT Pub. Date: Sep. 27, 2007

(65) Prior Publication Data
US 2010/0232662 A1    Sep. 16, 2010

(30) Foreign Application Priority Data
Mar. 23, 2006    (EP) ..................................... 06111614

(51) Int. Cl.
*G06K 9/00* (2006.01)
(52) U.S. Cl. .......................... 382/128; 382/131; 250/302
(58) Field of Classification Search .................. 382/128, 382/131; 250/302
See application file for complete search history.

(56) References Cited

U.S. PATENT DOCUMENTS

| | | | | |
|---|---|---|---|---|
| 4,301,140 A | * | 11/1981 | Frank et al. ................... | 424/1.73 |
| 5,459,769 A | * | 10/1995 | Brown ................................ | 378/4 |
| 5,687,208 A | * | 11/1997 | Bae et al. ............................ | 378/8 |
| 6,342,699 B1 | | 1/2002 | Jeanguillaume | |
| 7,127,095 B2 | * | 10/2006 | El Fakhri et al. .............. | 382/128 |
| 7,650,021 B2 | * | 1/2010 | Braess ........................... | 382/128 |
| 7,848,557 B2 | * | 12/2010 | Kadrmas et al. .............. | 382/131 |
| 2003/0004584 A1 | | 1/2003 | Hallett | |
| 2008/0253634 A1 | * | 10/2008 | Hay et al. ...................... | 382/130 |

OTHER PUBLICATIONS

Turkheimer et al., Modeling dynamic pet-spect studies in the wavelet domain, Journal of Cerebral Blood Flow and Metabolism, 20, 2000, pp. 879-893.*

Ichise et al., An introduction to pet and spect neuroreceptor quantification models, Nucl Med, 2001 pp. 755-763.*

(Continued)

*Primary Examiner* — Alexander H Taningco (57) ABSTRACT

A method within dynamic molecular imaging comprising dynamically estimating a first parameter ($\beta(x)$) and a second parameter ($k(x)$) of an activity function describing the bio distribution of an administered tracer, is disclosed. More specifically, the method comprises specifying a first target variance ($\sigma_{\beta,T}(x)$) and a second target variance ($\sigma_{\beta,T}(x)$) of the first parameter ($\beta(x)$) and the second parameter ($k(x)$) of the activity function, respectively; initiating an image acquisition; reconstructing the first parameter ($\beta(x)$) and the second parameter ($k(x)$); reconstructing a first associated variance ($\sigma_\beta(x)$) and a second associated variance ($\sigma_k(x)$) of the first parameter ($\beta(x)$) and the second parameter ($k(x)$), respectively; and repeating the image acquisition and the reconstructing until the first associated variance ($\sigma_\beta(x)$) and the second associated variance ($\sigma_k(x)$) are equal to or less than the first target variance ($\sigma_{\beta,T}(x)$) and the second target variance ($\sigma_{\beta,T}(x)$), respectively, $\sigma_\beta(x) \leq \sigma_{\beta,T}(x)$ and $\sigma_k(x) \leq \sigma_{\beta,T}(x)$. The method enables patient-specific adaptive protocols within molecular imaging.

15 Claims, 4 Drawing Sheets

OTHER PUBLICATIONS

Gullberg et al., Efficient estimation of dynamic cardiac spect kinetic parameters using weighted least squares estimates of dynamic reconstructions, Nuclear Science Symposium and Medical Imaging Conference IEEE, 1995, pp. 1684-1688.*

Bae et al., Multiphasic Injection Method for Uniform Prolonged Vascular Enhancement at CT Angiography: Pharmacokinetic Analysis and Experimental Porcine Model, Radiology, 2000, pp. 872-880.*

M. Kamasak,: et al: Direct Reconstruction of Kinetic Parameter Images from Dynamic PET Data, IEEE Trans Med Imaging 2005, Vol. 24, No. 5, May 2005, pp. 636-650.

D. Snyder, Parameter Estimation for Dynamic Studies in Emission-Tomography Systems Having List-Mode Data, IEEE Trans Nucl Sci 31, 1984, pp. 925-931.

Huesman, R.H. et al "Kinetic Data Analysis with a Noisy Input Function" Physics in Medicine and Biology, Taylor and Francis Ltd., vol. 32, No. 12, Dec. 1, 1987, pp. 1569-1570.

* cited by examiner

METHOD TO INDIVIDUALIZE KINETIC PARAMETER ESTIMATION FOR DYNAMIC MOLECULAR IMAGING PROCEDURES

This invention relates in general to the field of molecular imaging. More particularly, the invention relates to the adaptation of kinetic parameter estimation for dynamic molecular imaging procedures to individual patient anatomy and disease condition.

Molecular imaging is extensively used in medicine as a technique to image various targets or pathways, particularly in vivo. Tracers functioning as probes facilitate the imaging and chemically interact with their surroundings and in turn alter the image according to the molecular changes occurring within the area of interest. Molecular imaging is applied to many different areas of interest, such as determination of a pre-disease state or molecular states that occur prior to the occurrence or detection of typical symptoms of a disease. Other applications comprise the imaging of gene expression in vivo and the development of novel tracers or biomarkers.

In order to implement molecular imaging, there are currently several different molecular imaging systems and devices available, such as SPECT (Single Photon Emission Computed Tomography) systems and PET (Positron Emission Tomography) systems. The latter are important techniques when imaging physiological activities, as for instance in the brain or when determining flow paths in vivo. Typical molecular imaging devices continuously sample patient data in list mode, wherein list mode data means that single events in SPECT or coincidence events in PET are registered with a time stamp. List mode data is subsequently binned, reconstructed and the underlying kinetic parameters are estimated utilizing pharmacokinetic modeling techniques. Alternatively, list mode data is directly fed into the kinetic modeling engine utilizing direct parameter estimation techniques bypassing the binning and reconstruction steps.

With recent developments in multi-modal imaging equipment and novel targeted tracers, it has become feasible to objectively probe molecular processes, which are a key to understanding the underlying disease mechanisms, as well as the early assessment of treatment responses. Dynamic molecular imaging protocols are being used increasingly in the clinic, and kinetic modeling tools are being developed to improve estimation of the relevant molecular parameters. Examples for such molecular parameters are the flow rate of a tracer through tissue or blood, the trapping, wash-out and uptake rate of tracer into a tissue, or even reaction rates of the tracer undergoing chemical modifications.

There are basically three main approaches to the creation of parametric images: the "indirect approach", the "semi-direct approach" and the "direct approach", which are described in more detail hereinafter.

The indirect approach involves firstly reconstructing the registered images for each of the measurement times, and then estimating the kinetic parameters at each voxel. This method has the drawback of having a low signal-to-noise ratio of the time-activity curve for each voxel, which makes the accurate estimation of the parameters difficult.

The semi-direct approach attempts to improve the signal-to-noise ratio by constraining the possible choices of time-courses for each voxel via signal sub-spaces or splines. Spline-based methods have certain computational advantages when processing list mode data. However, it is a two-step process of first computing spline coefficients and then kinetic parameters, which results in a loss of optimality, especially when the number of spline coefficients is larger than the number of kinetic parameters.

The direct approach involves a direct way of reconstruction of kinetic parameters. Different direct estimation algorithms are for instance described by D. Snyder, "Parameter estimation for dynamic studies in emission-tomography systems having list-mode data" IEEE Trans Nucl Sci 31 (1984) pp 925-931; or Kamasak M E et al, "Direct reconstruction of kinetic parameter images from dynamic PET data, IEEE Trans Med Imaging (2005) May; 24(5): pp 636-650; which herein are incorporated by reference.

Today, design of dynamic imaging protocols is largely accomplished by trial and error. Once a good candidate protocol has been identified empirically, it is used for all patients in a blanket fashion without any consideration to inter-patient variability. These protocols usually specify the sampling scheme for image acquisition as well as the amount of tracer activity to be administered before scanning is initiated. However, tracer bio-kinetics depends greatly on the individual patient's anatomy and disease type leading to inter-patient variability in image quality and in a variance for the kinetic parameters being estimated. Moreover, consistent figures-of-merit measuring the quality of the estimated kinetic parameters are indispensable and an absolute prerequisite for establishing quality assurance procedures.

Thus, there is a need for a mechanism strategy, which adaptively takes into account the individual patient's anatomy and disease condition. Furthermore, it is anticipated that an optimally adapted dynamic imaging protocol allows for increased flexibility, time and cost-effectiveness as opposed to standard procedures, reducing the risk of false parameter settings and poor diagnostic results.

Hence, it is desired to provide an advantageous method within molecular imaging, for instance providing for patient-specific adaptive protocols.

Accordingly, the present invention preferably seeks to mitigate, alleviate or eliminate one or more of the above-identified deficiencies in the art and disadvantages singly or in any combination and solves at least the above-mentioned problems by providing a method, an apparatus, a system, a computer-readable medium, and a use of the apparatus according to the appended patent claims.

According to one aspect of the invention, a method is provided, within dynamic molecular imaging comprising dynamically estimating a first parameter $\beta(x)$ and a second parameter $k(x)$ of an activity function describing the bio distribution of an administered tracer. The method comprises specifying a first target variance $\sigma_{\beta,T}(x)$ and a second target variance $\sigma_{k,T}(x)$ of the first parameter $\beta(x)$ and the second parameter $k(x)$ of the activity function, respectively. Further the method comprises initiating an image acquisition; reconstructing the first parameter $\beta(x)$ and the second parameter $k(x)$; reconstructing a first associated variance $\sigma_\beta(x)$ and a second associated variance $\sigma_k(x)$ of the first parameter $\beta(x)$ and the second parameter $k(x)$, respectively. Moreover, the method comprises repeating the image acquisition and the reconstructing of the first parameter $\beta(x)$ and the second parameter $k(x)$ and the first associated variance $\sigma_\beta(x)$ and the second associated variance $\sigma_k(x)$ until the first associated variance $\sigma_\beta(x)$ and the second associated variance $\sigma_k(x)$ are equal to or less than the first target variance $\sigma_{\beta,T}(x)$ and the second target variance $(\sigma_{k,T}(x))$, respectively, $\sigma_\beta(x) \leq \sigma_{\beta,T}(x)$ and $\sigma_k(x) \leq \sigma_{k,T}(x)$.

According to yet another aspect of the invention, an apparatus is provided within dynamic molecular imaging provided to dynamically estimate a first parameter $\beta(x)$ and a second parameter $k(x)$ of an activity function describing the bio distribution of an administered tracer. The apparatus comprises a specifying means for specifying a first target variance $\sigma_{\beta,T}(x)$ and a second target variance $\sigma_{k,T}(x)$ of the first parameter $\beta(x)$ and the second parameter $k(x)$ of the activity function, respectively. The apparatus comprises further an initiating means for initiating an image acquisition; a first reconstructing means for reconstructing the first parameter $\beta(x)$ and the second parameter $k(x)$; a second reconstructing means for reconstructing a first associated variance $\sigma_\beta(x)$ and a second associated variance $\sigma_k(x)$ of the first parameter $\beta(x)$ and the second parameter $k(x)$, respectively; and a repeating means for repeating the image acquisition and the reconstructing of the first parameter $\beta(x)$ and the second parameter $k(x)$ and the first associated variance $\sigma_\beta(x)$ and the second associated variance $\sigma_k(x)$ until the first associated variance $\sigma_\beta(x)$ and the second associated variance $\sigma_k(x)$ are equal to or less than the first target variance $\sigma_{\beta,T}(x)$ and the second target variance $\sigma_{k,T}(x)$, respectively, $\sigma_\beta(x) \leq \sigma_{\beta,T}(x)$ and $\sigma_k(x) \leq \sigma_{k,T}(x)$.

According to yet another aspect of the invention, a molecular imaging system is provided, which comprises an apparatus according to the above-described aspect of the invention.

According to a further aspect of the invention, a computer-readable medium having embodied thereon a computer program for processing by a computer is provided. The computer program comprises a specification code segment for specifying a first target variance $\sigma_{\beta,T}(x)$ and a second target variance $\sigma_{k,T}(x)$ of the first parameter $\beta(x)$ and the second parameter $k(x)$ of the activity function, respectively; an initiation code segment for initiating an image acquisition; a first reconstruction code segment for reconstructing the first parameter $\beta(x)$ and the second parameter $k(x)$; a second reconstruction code segment for reconstructing a first associated variance $\sigma_\beta(x)$ and a second associated variance $\sigma_k(x)$ of the first parameter $\beta(x)$ and the second parameter $k(x)$, respectively; and a repetition code segment for repeating the image acquisition and the reconstructing of the first parameter $\beta(x)$ and the second parameter $k(x)$ and the first associated variance $\sigma_\beta(x)$ and the second associated variance $\sigma_k(x)$ until the first associated variance $\sigma_\beta(x)$ and the second associated variance $\sigma_k(x)$ are equal to or less than the first target variance $\sigma_{\beta,T}(x)$ and the second target variance $\sigma_{k,T}(x)$, respectively, $\sigma_\beta(x) \leq \sigma_{\beta,T}(x)$ and $\sigma_k(x) \leq \sigma_{k,T}(x)$.

According to yet a further aspect of the invention, a use of a method according to an aspect of the invention is provided. More precisely, the method is used for determining a pre-disease state or a molecular state that occurs prior to typical symptoms of a disease are detectable.

These and other aspects, features and advantages that the invention is capable of, will be apparent and elucidated from the following description of embodiments of the present invention, reference being made to the accompanying drawings, in which.

The following description focuses on embodiments of the present invention applicable to specific applications within dynamic molecular imaging. However, it will be appreciated that the invention is not limited to these specific applications or implementations, but may be applied to many other applications within the field of molecular imaging.

The present invention provides an advantageous way of improving estimation of the relevant molecular parameters, which may be the flow rate of a tracer through tissue or blood, the trapping, wash-out and uptake rate of tracer into a tissue, or even reaction rates of the tracer undergoing chemical modifications.

Moreover, the present invention provides a convenient foolproof way of establishing quality assurance procedures, which take into account the individual patient anatomy and disease type leading to inter-patient variability in image quality and in the variance for parameters being estimated.

Figure 1:
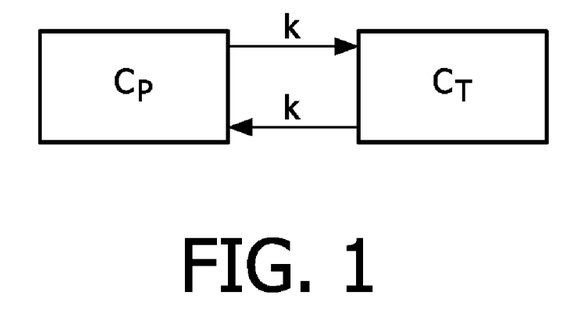
FIG. 1 is a schematic illustration of a pharmacokinetic two-compartment model comprising a tissue and a blood compartment.

FIG. 1 is showing a known pharmacokinetic compartment model comprising a tissue and a blood compartment. If for instance a dynamic SPECT measurement with $^{99m}$Tc-teboroxime is used to estimate myocardial perfusion, according to standard protocols, SPECT projections are acquired over 17 minutes after tracer injection. In FIG. 1, $C_P$ denotes the tracer concentration in the blood compartment, whereas $C_T$ specifies the concentration in the tissue compartment. In a pharmacokinetic two-compartment model, the total activity measured, involving a weighted sum of the individual concentrations associated to the compartments for a region of interest or an individual voxel at position x, is described for each point in time t by an activity function $A(x,t)=[1-\beta(x)] \cdot C_P + \beta(x) \cdot C_T$. The activity function $A(x,t)$ hence describes the biodistribution of the tracer. Here, parameter $\beta(x)$ denotes the partition of blood and tissue compartments at a position x in the region of interest. The region of interest may for instance be a human organ, such as the heart. The concentration in the tissue compartment, $C_T$, is composed of an inflow from a reservoir with corresponding tracer concentration $C_P$ (specified by the input function) by a rate k and the outflow of tracer by the same rate k. In mathematical terms this is given by a convolution of the input function with the "system function" of the tissue compartment $$C_T(x,t)=k(x) \cdot \exp[-k(x) \cdot t] \otimes C_P(x,t),$$

and hence $$A(x,t)=[1-\beta(x)] \cdot C_P(t)+\beta(x) \cdot k(x) \cdot C_P(t) \otimes e^{[-k(x) \cdot t]} \quad (1)$$

Here, $C_P$ is a known input function that for instance is sampled from arterial or venous blood, or extracted from a molecular image. To be able to determine the activity or concentration of the tracer in the region of interest, the parameters $\beta(x)$ and $k(x)$ need to be estimated. After running an optimization, such as an indirect, semi-direct or direct optimization, a spatial distribution or parametric map for $\beta(x)$ and $k(x)$ is obtained.

The optimization process may proceed in slightly different ways for the indirect, the semi-direct and the direct approach. The indirect approach features an estimate of $A(x,t)$ based on the list mode data; $\beta(x)$ and $k(x)$ are chosen to minimize the difference (e.g. sum-squared difference) between the estimated $A(x,t)$ and theoretical (true) value for $A(x,t)$ according to the compartment model described in Equation 1.

Optimization for the semi-direct approach is largely the same as the indirect approach, but with an extra step: a predefined function (e.g. a spline) is fitted to the estimated activity $A(x,t)$, yielding a smoothed approximation $\tilde{A}(x,t)$, and $\beta(x)$ and $k(x)$ are chosen to fit $\tilde{A}(x,t)$.

The direct approach is more involved, and includes choosing $\beta(x)$ and $k(x)$ to create the theoretical activity function $A(x,t)$, which most likely would have created the recorded list mode data (see e.g. D. Snyder, "Parameter estimation for dynamic studies in emission-tomography systems having list-mode data" IEEE Trans Nucl Sci 31 (1984) pp 925-931; or Kamasak M E et al, "Direct reconstruction of kinetic parameter images from dynamic PET data, IEEE Trans Med Imaging (2005) May; 24(5): pp 636-650) for a more detailed description.)

The variances $\sigma_\beta(x)$ and $\sigma_k(x)$ can be obtained in the same process, and depend on how strongly the fit of the modeled A(x,t) to the actual recording, i.e. the difference between the recorded A(x,t) and the adapted Ã(x,t) or the likelihood of the modeled A(x,t) given the list mode data, deteriorates when $\beta(x)$ and k(x) are varied around their optimal values.

Figure 2:
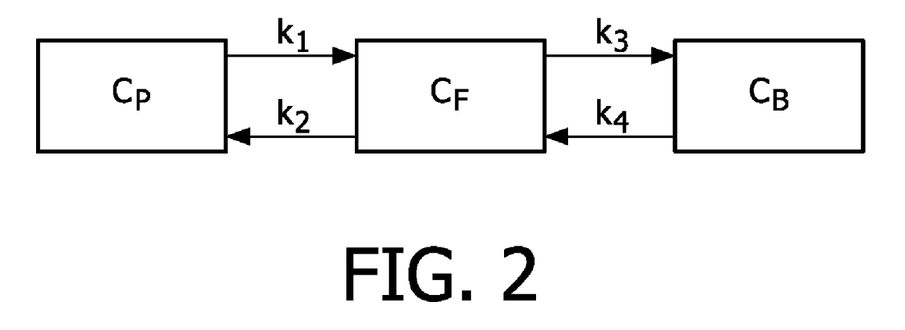
FIG. 2 is a schematic illustration of a pharmacokinetic multi-compartment model.

The activity function including the parameters $\beta(x)$ and k(x) describes the activity and hence indirectly the concentration of the administered tracer. The activity function and hence the parameters vary with the selected compartment model. FIG. 2 shows an exemplary pharmacokinetic multi-compartment model, in which $k_1$, $k_2$, $k_3$ and $k_4$ describe the tracer exchange rates between compartments. $C_P$ describes the molar concentration of tracer in the plasma, $C_F$ describes the molar concentration of unbound tracer, and $C_B$ describes is the molar concentration of metabolized or bound tracer.

The steps commonly used in dynamic tracer-studies with an emission-tomography list-mode data system are:
(a) collecting data for successive time frames;
(b) reconstructing images at each interval or time frame, thereby providing the estimated spatial-activity distribution as a function of time;
(c) identifying in each image the region of interest for the dynamic study;
(d) weighting each list-mode data point by a factor that accounts for its contribution to the region of interest before integrating each image over the region of interest to get the cumulative activity in the region of interest in each frame; and
(e) estimating parameters from the reconstructed activity images produced in step (d). In the case direct parameter estimation is deployed, meaning that list-mode data is directly reconstructed into kinetic parameters, standard acquisition protocols for a certain clinical task, such as imaging the myocardial perfusion are used, which do not adapt to patient specifics, such as weight and size and other individual attributes. The disadvantage of prior art is that the scanning time and/or the activity administered is not adapted on an individualized basis, hence, the parameters are estimated with great variation in confidence.

The following description focuses on embodiments of the present invention applicable to a dynamic molecular imaging system, wherein the scan time is used as the parameter to be adaptively modified on an individualized basis. In this way it is possible to individualize kinetic parameter estimation by adaptively changing the involved kinetic parameters.

The kinetic parameters that are necessary for the protocol depend on which compartment model is used to describe the tracer system. In the general case, the activity function for a voxel at position x at a point in time t is given by $A(x,t;\bar{v}(x))$, where $\bar{v}(x)$ represents the full set of free model parameters.

The selection of compartment model depends on the studied process. For a perfusion process, one need a very specific compartmental model, which comprises a blood compartment and a tissue compartment, whose exchange of tracer is described by a single kinetic parameter k. In general applications, where two compartmental models are deployed, the kinetic parameters describing the transport between the compartments may vary, therefore requiring the introduction of kinetic parameters $k_1$ and $k_2$. One may choose the above-mentioned perfusion compartment model purposely for the sake of simplicity, as this is the simplest case for a compartment model, with only two free parameters describing a clinically relevant application. However, the concept of the invention is applicable to any compartmental topology and any number of free parameters and is hence not limited to the above-mentioned perfusion compartment model.

The spatial resolution of the scanner systems offered today (e.g. SPECT and PET) is such that there is always a mixture of tissue and blood sub-compartments in a pixel or voxel, and therefore the parameter $\beta(x)$ will remain in currently used general two compartmental or a multi compartmental models. However, it is envisaged that with future molecular image acquisition systems offering higher resolution, the parameter $\beta(x)$ will be obsolete.

Figure 3:
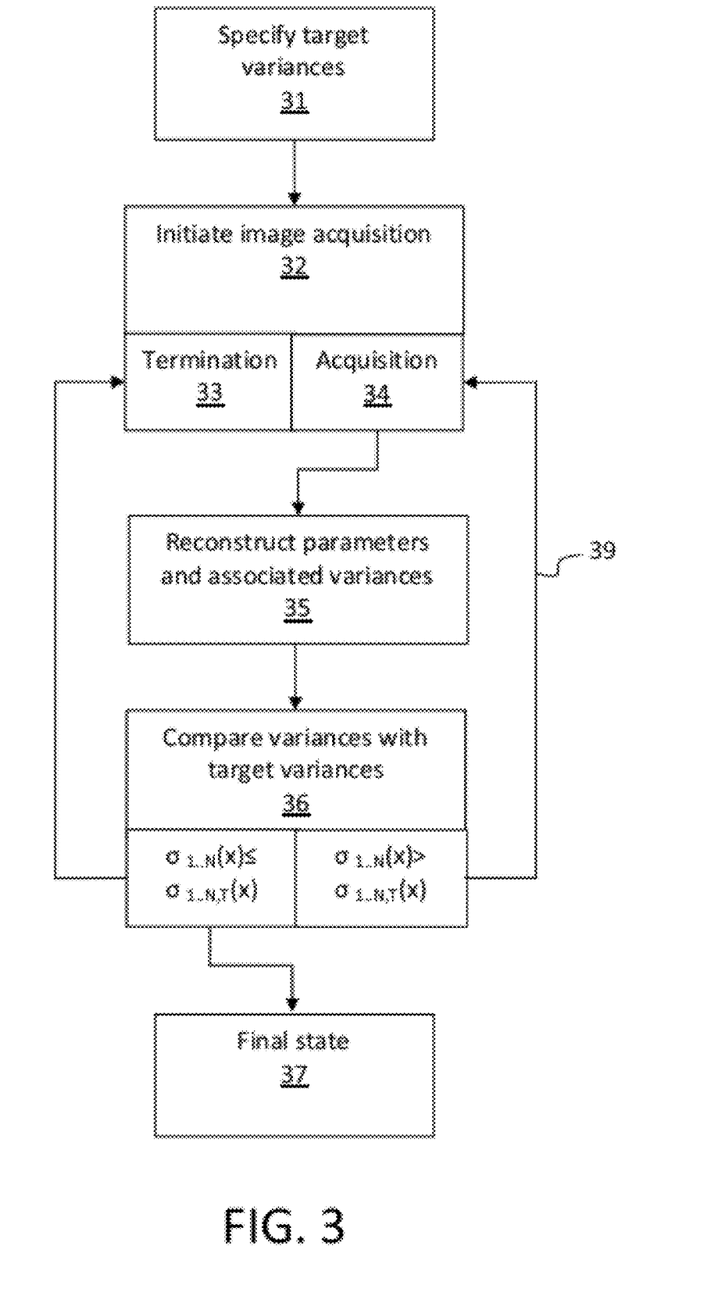
FIG. 3 is a process flow chart illustrating an embodiment of the method of the present invention.

An embodiment of the present invention, according to FIG. 3, relates to a method for estimating kinetic parameters on an individualized basis.

The method is summarized in the following steps, wherein step 31 comprises specification of target confidence intervals ($\sigma_{\beta,T}(x)$ and $\sigma_{k,T}(x)$ for a two-compartment model) for the parameters necessary for the protocol, either locally, e.g. for a small region of tissue or a specific region of interest, or globally, the same for each voxel position x.

In step 32 of the embodied method, an image acquisition is initiated concurrently with data acquisition step 34 to estimate parameters $\beta(x)$ and k(x) for the region delineated using a direct parameter estimation algorithm in step 35, and associated variances $\sigma_\beta(x)$ and $\sigma_k(x)$, see definition below, for the parameters $\beta(x)$ and k(x), respectively, see derivation below. The image acquisition is continuously collecting image data, e.g. in list mode. Image acquisition may for instance be performed by a PET or SPECT scanner, "scanning" an image in a way known to the skilled person.

In step 36 of the embodied method, if $\sigma_\beta(x)>\sigma_{\beta,T}(x)$ or $\sigma_k(x)>\sigma_{k,T}(x)$, after an iteration step of the direct parameter estimation algorithm, recently acquisitioned data from data acquisition in step 34 are added to the list mode data and the direct parameter estimation algorithm re-estimates in the next iteration step 39 the parameters $\beta(x)$ and k(x) and the corresponding associated variances $\sigma_\beta(x)$ and $\sigma_k(x)$.

Finally, in step 33 of the embodied method, the data acquisition is terminated when the associated variances $\sigma_\beta(x)$ and $\sigma_k(x)$ have reached the target variances $\sigma_{\beta,T}(x)$ and $\sigma_{k,T}(x)$, respectively, i.e. when $\sigma_\beta(x) \leq \sigma_{\beta,T}(x)$ and $\sigma_k(x) \leq \sigma_{k,T}(x)$. In this final state 37 the estimated parameters $\beta(x)$ and k(x) are of sufficient accuracy regardless of inter-patient variability in order to produce a high quality molecular image of the region of interest.

Most procedures for direct estimation are based on maximizing a likelihood function $P(\beta(x),k(x)|D)$, where P denotes the probability distribution for the parameters $\beta(x)$ and k(x) given the observed list mode data. The probability distribution P does not have one of the standard Gaussian or Gamma forms, due to the non-linear behavior of the activity function, and further non-linearities that arise in the expression of $P(\beta(x),k(x)|D)$. A standard approach in these situations is to approximate this complicated probability distribution with a Gaussian distribution. The mean of this distribution is at:
$[(\beta'(x),k'(x)] = \arg\max(P(\beta(x),k(x)|D))$.

In an embodiment of the invention the probability distribution P is approximated with a Gaussian distribution. This embodiment is less computationally demanding.

In another embodiment of the invention the probability distribution P is approximated with a Gamma distribution. This embodiment is less computationally demanding.

According to an embodiment of the invention the associated variances $\sigma_\beta(x)$ and $\sigma_k(x)$ are defined as:

$$\sigma_\beta(x) = \frac{\partial^2}{\partial \beta(x)^2}[P(\beta(x), k(x) | D)]\bigg|_{\beta(x)=\beta'(x), k(x)=k'(x)}, \text{ and}$$

$$\sigma_k(x) = \frac{\partial^2}{\partial k(x)^2}[P(\beta(x), k(x) | D)]\bigg|_{\beta(x)=\beta'(x), k(x)=k'(x)}.$$

The above associated variance expressions represent the second derivatives of the exact probability distribution with respect to the kinetic parameters, taken at its maximum. These two quantities give a good approximation of the actual variance, and can therefore be used as confidence intervals, as in the method of the invention.

In another embodiment of the invention, the parameters β(x) and k(x) and the associated variances $\sigma_\beta(x)$ and $\sigma_k(x)$ may be any parameters associated with molecular imaging, such as a kinetic or non-kinetic parameter.

In another embodiment of the invention, at least one of the parameters β(x) and k(x) is a kinetic parameter.

In another embodiment of the invention, the method is applied to an arbitrary pharmacokinetic compartment model, such as a pharmacokinetic two-compartment model or a pharmacokinetic multi-compartment model or any other model for determination of the corresponding kinetic parameters.

According to another embodiment of the invention any optimization algorithm, such as direct, indirect or semi direct parameter estimation algorithm for estimating the parameters of the activity function, and hence the bio distribution of the tracer(s), may be used.

Figure 4:
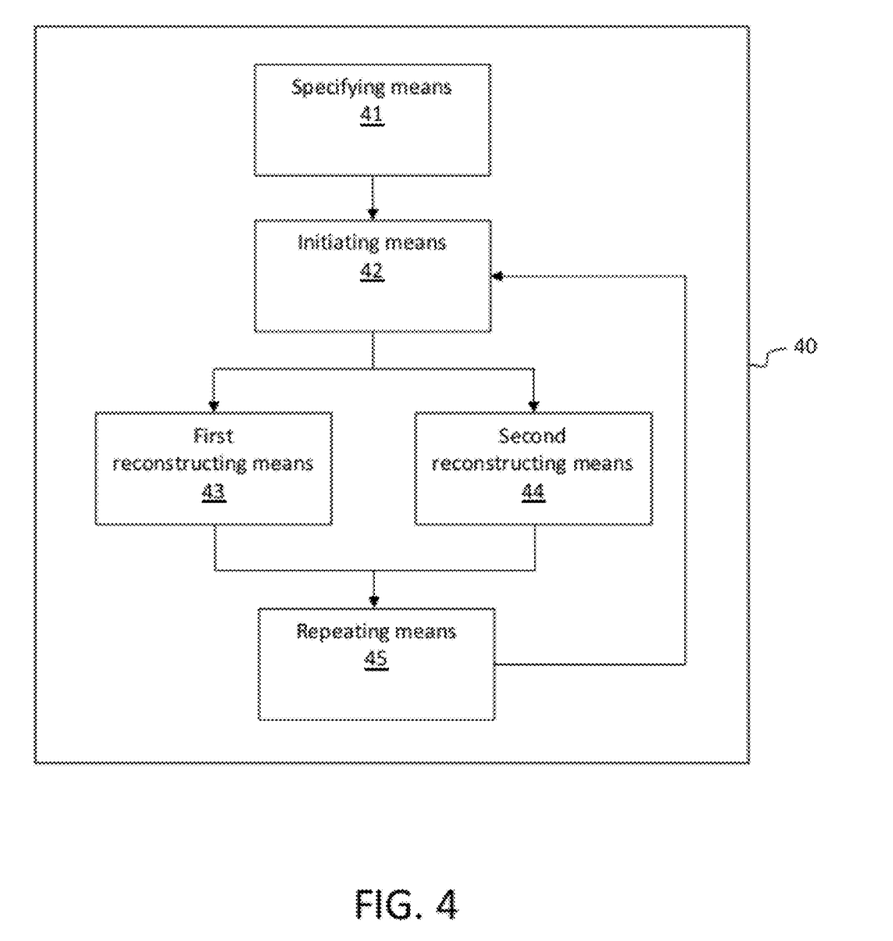
FIG. 4 is a schematic illustration that illustrates an embodiment of an apparatus of the present invention.

According to an embodiment of the invention, according to FIG. 4, an apparatus 40 within dynamic molecular imaging is provided to dynamically estimate a first parameter β(x) and a second parameter k(x) of an activity function describing the bio distribution of an administered tracer, wherein the apparatus comprises a specifying means 41, an initiating means 42, a first reconstructing means 43, a second reconstructing means 44 and a repeating means 45. The specifying means 41 is provided to specify a first target variance $\sigma_{\beta,T}(x)$ and a second target variance $\sigma_{k,T}(x)$ of the first parameter β(x) and the second parameter k(x) of the activity function, respectively. These target variances may for instance be calculated from the second derivatives of the exact probability distribution, as explained above. The initiating means 42 is provided to initiate an image acquisition, in which image data is recorded continuously. The initiating means 42 is connected to the first reconstructing means 43, which is provided to reconstruct the first parameter β(x) and the second parameter k(x), based on the acquisitioned image data set so far collected by the image acquisition means 41. The initiating means 42 is also connected to the second reconstructing means 44, which is provided to reconstruct a first associated variance $\sigma_\beta(x)$ and a second associated variance $\sigma_k(x)$ of the first parameter β(x) and the second parameter k(x), respectively, based on the same acquisitioned image data set so far collected by the image acquisition means. The repeating means 45 is provided to decide whether the associated variances $\sigma_\beta(x)$ and $\sigma_k(x)$ is acceptable compared to the target variances $\sigma_{\beta,T}(x)$ and $\sigma_{k,T}(x)$, respectively. If $\sigma_\beta(x) > \sigma_{\beta,T}(x)$ or $\sigma_k(x) > \sigma_{k,T}(x)$ the repeating means 45 is provided to send a repeat signal to the initiating means 42 and first reconstructing means 43 and second reconstructing means 44 to repeat the parameter estimation. If $\sigma_\beta(x) \leq \sigma_{\beta,T}(x)$ and $\sigma_k(x) \leq \sigma_{k,T}(x)$ the repeating means is provided to terminate the parameter estimation.

In an embodiment of the invention an apparatus is provided to carry out the method of the invention.

According to another embodiment of the invention, an apparatus for use in molecular imaging is provided, that by estimating molecular parameters, provides determination of a pre-disease state or molecular states occurring prior to the detection of typical symptoms of a disease.

According to an embodiment of the invention the apparatus is comprised in a PET system or a SPECT system comprising molecular image acquisition means connected to the initiating means for initiating an image acquisition.

According to an embodiment of the invention the apparatus is a medical workstation.

In an embodiment of the invention a system comprising the apparatus according to the invention is provided.

Figure 5:
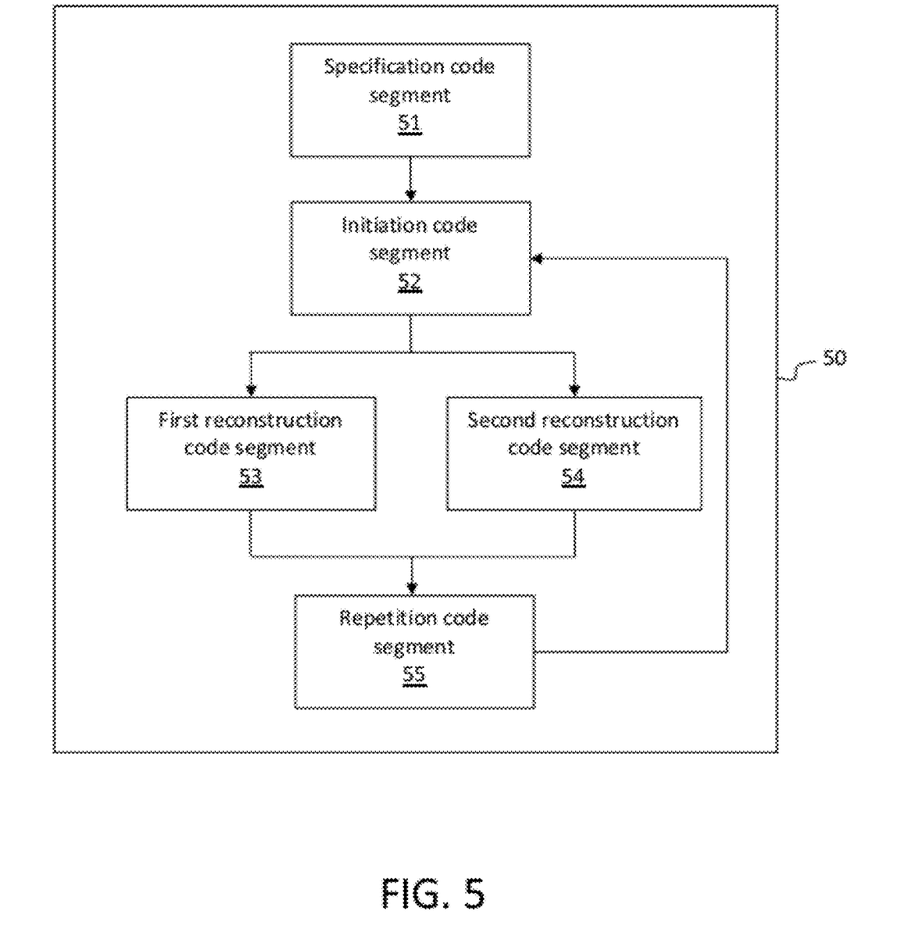
FIG. 5 is a schematic illustration that shows a computer program flow-chart illustrating a further embodiment of the present invention.

In an embodiment of the invention, according to FIG. 5, a computer-readable medium having embodied thereon a computer program 50 for processing by a computer, where the computer program 50 comprises a specification code segment 51, an initiation code segment 52, a first reconstruction code segment 53, a second reconstruction code segment 54, and a repetition code segment 55, is provided. The specification code segment 51 enables specifying a first target variance $\sigma_{\beta,T}(x)$ and a second target variance $\sigma_{k,T}(x)$ of the first parameter β(x) and the second parameter k(x) of an activity function, respectively. The initiation code segment 52 enables initiating an image acquisition. The first reconstruction code segment 53 enables reconstructing the first parameter β(x) and the second parameter k(x). The second reconstruction code segment 54 enables reconstructing a first associated variance $\sigma_\beta(x)$ and a second associated variance $\sigma_k(x)$ of the first parameter β(x) and the second parameter k(x), respectively. The repetition code segment 55 enables repeating the image acquisition and the reconstructing until the first associated variance $\sigma_\beta(x)$ and the second associated variance $\sigma_k(x)$ are equal to or less than the first target variance $\sigma_{\beta,T}(x)$ and the second target variance $\sigma_{k,T}(x)$, respectively, $\sigma_\beta(x) \leq \sigma_{\beta,T}(x)$ and $\sigma_k(x) \leq \sigma_{k,T}(x)$.

In another embodiment of the invention a computer-readable medium having embodied thereon a computer program for processing by a computer, is provided, where the computer program is able to carry out the method of the invention.

The invention may be implemented in any suitable form including hardware, software, firmware or any combination of these. However, preferably, the invention is implemented as computer software running on one or more data processors and/or digital signal processors. The elements and components of an embodiment of the invention may be physically, functionally and logically implemented in any suitable way. Indeed, the functionality may be implemented in a single unit, in a plurality of units or as part of other functional units. As such, the invention may be implemented in a single unit, or may be physically and functionally distributed between different units and processors.

Although the present invention has been described above with reference to specific embodiments, it is not intended to be limited to the specific form set forth herein. Rather, the invention is limited only by the accompanying claims and, other embodiments than the specific above are equally possible within the scope of these appended claims, e.g. different fields of application than those described above.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. A method executable in a molecular imaging system for dynamic molecular imaging comprising dynamically estimating a first parameter ($\beta(x)$) and a second parameter ($k(x)$) of an activity function describing the bio-distribution of an administered tracer, the method comprising:
    specifying a first target variance ($\sigma_{\beta,T}(x)$) and a second target variance ($\sigma_{k,T}(x)$) of the first parameter ($\beta(x)$) and the second parameter ($k(x)$) of the activity function, respectively;
    initiating an image acquisition;
    reconstructing the first parameter ($\beta(x)$) and the second parameter ($k(x)$);
    reconstructing a first associated variance ($\sigma_\beta(x)$) and a second associated variance ($\sigma_k(x)$) of the first parameter ($\beta(x)$) and the second parameter ($k(x)$), respectively; and
    repeating the image acquisition and the reconstructing of the first parameter ($\beta(x)$) and the second parameter ($k(x)$) and the first associated variance ($\sigma_\beta(x)$) and the second associated variance ($\sigma_k(x)$) until the first associated variance ($\sigma_\beta(x)$) and the second associated variance ($\sigma_k(x)$) are equal to or less than the first target variance ($\sigma_{\beta,T}(x)$) and the second target variance ($\sigma_{k,T}(x)$), respectively.

2. The method according to claim 1, wherein, if the first associated variance ($\sigma_\beta(x)$) is larger than the first target variance ($\sigma_{\beta,T}(x)$), $\sigma_\beta(x) > \sigma_{\beta,T}(x)$, or the second associated variance ($\sigma_k(x)$) is larger than the second target variance ($\sigma_{k,T}(x)$), $\sigma_k(x) > \sigma_{k,T}(x)$, after reconstructing a first associated variance ($\sigma_\beta(x)$) and a second associated variance ($\sigma_k(x)$) of the first parameter ($\beta(x)$) and the second parameter ($k(x)$), respectively, the image acquisition is repeated.

3. The method according to claim 1, wherein the reconstructing the first parameter ($\beta(x)$) and the second parameter ($k(x)$) uses a direct parameter estimation algorithm.

4. The method according to claim 3, wherein the direct parameter estimation algorithm is based on the expression of $P(\beta(x),k(x)|D)$, in which P denotes a probability distribution for the first parameter ($\beta(x)$) and the second parameter ($k(x)$) given the observed list-mode data D.

5. The method according to claim 4, wherein the first associated variance and the second associated variance are defined as:

$$\sigma_\beta(x) = \frac{\partial^2}{\partial \beta(x)^2}[P(\beta(x),k(x)|D)]\Big|_{\beta(x)=\beta'(x),k(x)=k'(x)}, \text{ and}$$

$$\sigma_k(x) = \frac{\partial^2}{\partial k(x)^2}[P(\beta(x),k(x)|D)]\Big|_{\beta(x)=\beta'(x),k(x)=k'(x)}, \text{ respectively.}$$

6. The method according to any of the claim 4, wherein the probability distribution P is approximated with a Gaussian or Gamma distribution.

7. The method according to any of the claim 3, wherein the first and second parameters are determined using the direct parameter estimation algorithm adapted to a two-compartment model.

8. The method according to any of the claim 3, wherein the first and second parameters are determined using the direct parameter estimation algorithm adapted to a multi-compartment model.

9. The method according to claim 1, wherein the activity function ($A(x,t)$) is defined for a two-compartment model as:
$$A(x,t)=[1-\beta(x)]\cdot C_P(t)+\beta(x)\cdot k(x)\cdot C_P(t) \otimes e^{[-k(x)\cdot t]},$$
in which $C_P$ is a known input function describing tracer concentration in plasma.

10. The method according to claim 1, wherein the first parameter ($\beta(x)$) or the second parameter ($k(x)$) is a kinetic parameter.

11. Use of a method according to claim 1 for determining a pre-disease state or a molecular state that occurs prior to typical symptoms of a disease are detectable.

12. An apparatus within dynamic molecular imaging provided to dynamically estimate a first parameter ($\beta(x)$) and a second parameter ($k(x)$) of an activity function describing the bio distribution of an administered tracer, the apparatus comprising:
    a specifying means for specifying a first target variance ($\sigma_{\beta,T}(x)$) and a second target variance ($\sigma_{k,T}(x)$) of the first parameter ($\beta(x)$) and the second parameter ($k(x)$) of the activity function, respectively;
    an initiating means for initiating an image acquisition;
    a first reconstructing means for reconstructing the first parameter ($\beta(x)$) and the second parameter ($k(x)$);
    a second reconstructing means for reconstructing a first associated variance ($\sigma_\beta(x)$) and a second associated variance ($\sigma_k(x)$) of the first parameter ($\beta(x)$) and the second parameter ($k(x)$), respectively; and
    a repeating means for repeating the image acquisition and the reconstructing of the first parameter ($\beta(x)$) and the second parameter ($k(x)$) and the first associated variance ($\sigma_\beta(x)$) and the second associated variance ($\sigma_k(x)$) until the first associated variance ($\sigma_\beta(x)$) and the second associated variance ($\sigma_k(x)$) are equal to or less than the first target variance ($\sigma_{\beta,T}(x)$) and the second target variance ($\sigma_{k,T}(x)$), respectively, $\sigma_\beta(x) \leq \sigma_{\beta,T}(x)$ and $\sigma_k(x) \leq \sigma_{k,T}(x)$.

13. The apparatus according to claim 12, wherein the apparatus is comprised in a PET system or a SPECT system comprising molecular image acquisition means connected to the initiating means for initiating an image acquisition.

14. The apparatus according to claim 12, wherein the apparatus is a medical workstation.

15. A non-transitory computer-readable medium having embodied thereon a computer program for processing by a computer, the computer medium comprising:
    a specification code segment for specifying a first target variance ($\sigma_{\beta,T}(x)$) and a second target variance ($\sigma_{k,T}(x)$) of the first parameter ($\beta(x)$) and the second parameter ($k(x)$) of the activity function, respectively;
    an initiation code segment for initiating an image acquisition;
    a first reconstruction code segment for reconstructing the first parameter ($\beta(x)$) and the second parameter ($k(x)$);
    a second reconstruction code segment for reconstructing a first associated variance ($\sigma_\beta(x)$) and a second associated variance ($\sigma_k(x)$) of the first parameter ($\beta(x)$) and the second parameter ($k(x)$), respectively; and
    a repetition code segment for repeating the image acquisition and the reconstructing of the first parameter ($\beta(x)$) and the second parameter ($k(x)$) and the first associated variance ($\sigma_\beta(x)$) and the second associated variance ($\sigma_k(x)$) until the first associated variance ($\sigma_\beta(x)$) and the second associated variance ($\sigma_k(x)$) are equal to or less than the first target variance ($\sigma_{\beta,T}(x)$) and the second target variance ($\sigma_{k,T}(x)$), respectively, $\sigma_{k,T}(x) \leq \sigma_{\beta,T}(x)$ and $\sigma_k(x) \leq \sigma_{k,T}(x)$.

* * * * *